United States Patent
Kruger

(10) Patent No.: US 9,468,610 B2
(45) Date of Patent: Oct. 18, 2016

(54) 1-AMINOCYCLOHEXANE DERIVATIVES FOR THE TREATMENT OF HEARING LOSS

(75) Inventor: Hagen Kruger, Frankfurt am Main (DE)

(73) Assignee: MERZ PHARMA GmbH & CO. KGaA, Frankfurt am Main (DE)

(*) Notice: Subject to any disclaimer, the term of this patent is extended or adjusted under 35 U.S.C. 154(b) by 0 days.

(21) Appl. No.: 12/733,582

(22) PCT Filed: Sep. 10, 2008

(86) PCT No.: PCT/EP2008/007419
§ 371 (c)(1),
(2), (4) Date: Aug. 2, 2010

(87) PCT Pub. No.: WO2009/033650
PCT Pub. Date: Mar. 19, 2009

(65) Prior Publication Data
US 2010/0298440 A1   Nov. 25, 2010

Related U.S. Application Data

(60) Provisional application No. 60/993,396, filed on Sep. 12, 2007, provisional application No. 61/066,931, filed on Feb. 25, 2008, provisional application No. 61/067,026, filed on Feb. 25, 2008, provisional application No. 61/067,083, filed on Feb. 25, 2008.

(30) Foreign Application Priority Data

Sep. 12, 2007 (EP) .................................. 07253630
Mar. 14, 2008 (EP) .................................. 08004776
Mar. 14, 2008 (EP) .................................. 08004777
Mar. 14, 2008 (EP) .................................. 08004778

(51) Int. Cl.
*A61K 31/13* (2006.01)
*A61K 9/20* (2006.01)

(52) U.S. Cl.
CPC ............. *A61K 31/13* (2013.01); *A61K 9/2054* (2013.01)

(58) Field of Classification Search
USPC .............................................. 514/579; 3/579
See application file for complete search history.

(56) References Cited

U.S. PATENT DOCUMENTS

| | | | |
|---|---|---|---|
| 6,034,134 A | 3/2000 | Gold | |
| 6,071,966 A | 6/2000 | Gold et al. | |
| 2003/0236286 A1 | 12/2003 | Deorazio | |
| 2006/0002999 A1* | 1/2006 | Yang et al. | 424/464 |
| 2006/0205789 A1* | 9/2006 | Lobl et al. | 514/326 |
| 2007/0141148 A1 | 6/2007 | Hauptmeier et al. | |

FOREIGN PATENT DOCUMENTS

| | | |
|---|---|---|
| WO | WO9810757 | 3/1998 |
| WO | WO2004043899 | 5/2004 |
| WO | WO 2005/044228 | 5/2005 |
| WO | WO 2006/069294 | 6/2006 |
| WO | WO2006079055 | 7/2006 |
| WO | WO 2006/096194 | 9/2006 |
| WO | WO 2007/009326 | 1/2007 |
| WO | WO2007062815 | 6/2007 |

OTHER PUBLICATIONS

Chen et al. Hearing Research 2001, 154, 108-115.*
Lynch et al. Drug Discover Today 2005, 10, 1291-1298.*
European Search Report for 07253630.3 of Dec. 27, 2007.
International Search Report and Written Opinion for PCT/EP2008/007419 of Nov. 20, 2008.
Chen, et al., Hearing Research, 2001, 154, 108-115.
Danysz, et al., Curr. Pharm. Des., 2002, 8, 835-843, Amino-alkyl-cyclohexanes as a novel class of uncompetitve NMDA receptor antagonists.
Enciclopedia of Drugs, M., RLS, 2001, p. 1012, 136.
Kos, et al., J. Pharmacol. Exp. Ther., 2006, 318, 1128-1136, Enhancement of antidepressant-like effects but not brain-derived neurotrophic factor mRNA expression by the novel N-methyl-D-aspartate receptor antagonist neramexane in mice.
Medicine Guide "The Merck Manual", M. "MIR", 1997, vol. 2, pp. 543-544.
Eggermont, et al., Drug Discovery Today, 2005, 10, 1283-1290.
European Search Report for European Appiication No. 08004776.4 of May 21, 2008.
European Search Report for European Application No. 08004777.2 of Jul. 2, 2008.
European Search Report for European Application No. 08004778.0 of Aug. 5, 2008.
Plazas, et al., Eur. J. Pharmacol., 2007, 566, 11-19.

* cited by examiner

*Primary Examiner* — Jeffrey S Lundgren
*Assistant Examiner* — Michael Schmitt
(74) *Attorney, Agent, or Firm* — Hueschen and Sage

(57) ABSTRACT

The present invention relates to the treatment of an individual diagnosed with hearing loss comprising administering to the individual an effective amount of a 1-amino-alkylcyclohexane derivative.

10 Claims, 1 Drawing Sheet

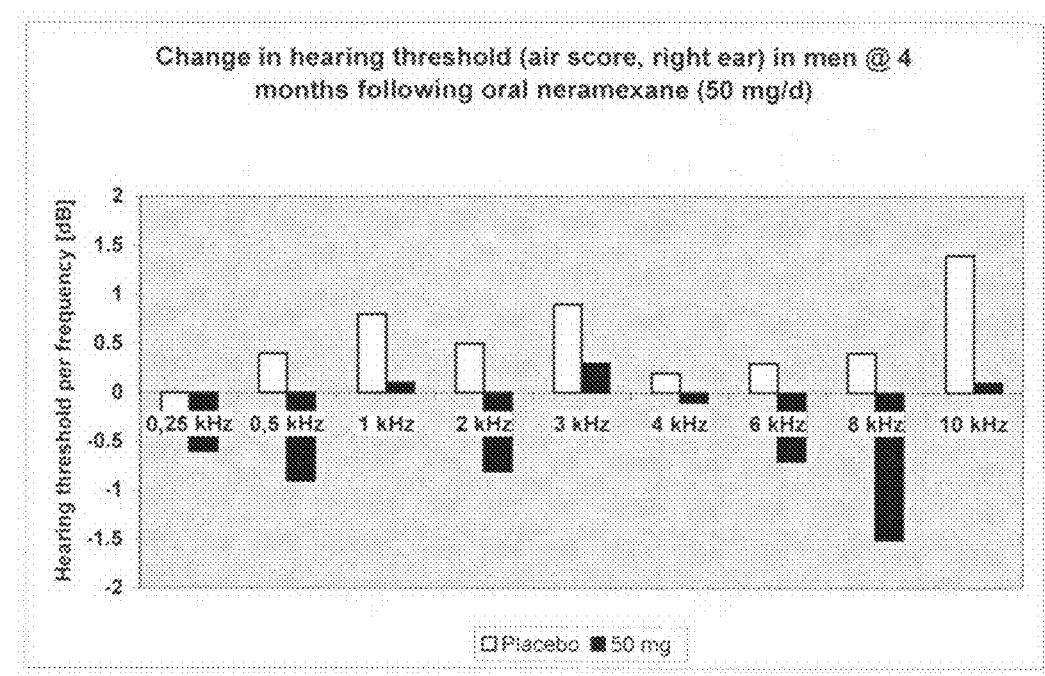

1-AMINOCYCLOHEXANE DERIVATIVES FOR THE TREATMENT OF HEARING LOSS

FIELD OF THE INVENTION

The present invention relates to the treatment of an individual diagnosed with hearing loss comprising administering to the individual an effective amount of a 1-aminoalkylcyclohexane derivative.

BACKGROUND OF THE INVENTION

This invention relates to methods of treating patients suffering from hearing loss and preventing patients from hearing loss.

Hearing loss and/or hearing impairment may be caused by a wide range of biological and environmental factors. Hearing loss also has a varied and complex etiology. Forms of hearing loss/hearing impairment include acoustic trauma, noise-induced hearing loss, sensorineural hearing loss, mixed hearing loss, unspecified hearing loss, ototoxic hearing loss, drug-induced hearing loss, environmental chemicals-induced hearing loss, cancer-induced hearing loss, surgical-induced hearing loss, radiation-induced hearing loss, infection-induced hearing loss, sudden (idiopathic) hearing loss, auditory processing disorder, and presbycusis.

Noise-induced hearing loss may be caused by acute or chronic conditions. Long-term exposure to excessive noise is the more common cause of noise-induced hearing loss; however, such hearing loss may also be caused by extremely loud sounds.

Sensorineural hearing loss is due to insensitivity of the inner ear or to impairment of function in the auditory nervous system. Sensorineural hearing loss may be caused by abnormalities in the hair cells of the organ of the Corti in the cochlea.

Ototoxic hearing loss may be caused by medications which damage the ear (i.e., drug-induced hearing loss). Such medications include chemotherapeutic (i.e., anti-neoplastics or anti-cancer) agents (such as cisplatin), aminoglycosides (such as gentamicin), diuretics (such as bumetanide), salicylates (such as aspirin), quinines, NSAIDS, and macrolide antibiotics.

Environmental chemicals-induced hearing loss may be caused by agents (i.e., environmental chemicals) which damage the ear (such as butyl nitrite, mercury or toluene).

Cancer-induced hearing loss may be caused by tumors in the middle ear as well as by other cancers which involve the ear and/or brain.

Surgical-induced hearing loss may occur after otologic or non-otologic surgery; however, the mechanism(s) associated with such hearing loss are not clear.

Radiation-induced hearing loss may be caused by intentional (for example, in radiation therapy) or unintentional exposure to radiation.

Infection-induced hearing loss may be caused by infections involving the inner ear and hearing nerve as well as by infections involving the middle ear. Moreover, there are a number of other types of infections (e.g., mumps, lyme disease, meningitis, herpesvirus infections, fungal infections, bacterial infections, AIDS, and tuberculosis) which may result in hearing loss.

Presbycusis appears to be related, in part, to noise exposure and is characterized by a stiffening of the basilar membrane and deterioration of the hair cells, stria vasularis, ganglion cells, and cochlear nuclei.

Certain drugs (i.e., nicergoline (US Published Application No. 2007/0123555), citalopram (Cruz, et al., *Laryngoscope*, 2004, 114, 1656-1659), L-carnitine (Derin, et al., *Clin. Otolaryngol.*, 2004, 29, 238-241), and D-methionine (Campbell, et al., *Hearing Reasearch*, 1996, 102, 90-98)), have been suggested as possible treatments for various types of hearing loss; however, a need exists for pharmaceutical products and improved methods for treatment of hearing loss.

1-Amino-alkylcyclohexanes such as neramexane (also known as 1-amino-1,3,3,5,5-pentamethylcyclohexane) have been found to be useful in the therapy of various diseases especially in certain neurological diseases, including Alzheimer's disease and neuropathic pain. 1-Amino-alkylcyclohexanes such as neramexane are disclosed in detail in U.S. Pat. Nos. 6,034,134 and 6,071,966, the subject matter of which patents is hereby incorporated by reference. It is believed that the therapeutic action of 1-amino-alkylcyclohexanes such as neramexane is related to the inhibition of the effects of excessive glutamate at the N-methyl-D-aspartate (NMDA) receptors of nerve cells, for which reason the compound is also categorized as an NMDA antagonist, or NMDA receptor antagonist. More specifically, neramexane appears to be a low to moderate-affinity, non-competitive NMDA-receptor antagonist believed to selectively block the excitotoxic effects associated with abnormal transmission of glutamate.

U.S. Pat. No. 6,034,134 discloses that 1-amino-alkylcyclohexanes may be useful in the treatment of tinnitus due to their activity as NMDA receptor antagonists.

SUMMARY OF THE INVENTION

The present invention relates to the treatment of an individual diagnosed with hearing loss, comprising administering to the individual an effective amount of a 1-aminoalkylcyclohexane derivative (e.g., neramexane).

A further aspect of the invention relates to the use of a 1-amino-alkylcyclohexane derivative (e.g., neramexane) for the manufacture of a medicament for treatment of an individual diagnosed with hearing loss.

A further aspect of the invention relates to a method of treating or preventing hearing loss in a subject in need thereof, comprising administering an effective amount of a 1-amino-alkylcyclohexane derivative (e.g., neramexane) in a pharmaceutically acceptable carrier.

A further aspect of the invention relates to such a method, wherein the hearing loss is selected from mild hearing loss, moderate hearing loss, severe hearing loss, profound hearing loss, and deafness.

A further aspect of the invention relates to such a method, wherein the hearing loss is selected from acoustic trauma, noise-induced hearing loss, sensorineural hearing loss, mixed hearing loss, unspecified hearing loss, ototoxic hearing loss, drug-induced hearing loss, environmental chemicals-induced hearing loss, cancer-induced hearing loss, surgical-induced hearing loss, radiation-induced hearing loss, infection-induced hearing loss, sudden (idiopathic) hearing loss, auditory processing disorder, and presbycusis.

A further aspect of the invention relates to such a method wherein the 1-amino-alkylcyclohexane derivative is neramexane mesylate.

A further aspect of the invention relates to such a method, wherein neramexane mesylate is administered in a range from about 5 mg to about 150 mg/day or wherein neramexane mesylate is administered in a range from about 5 mg to about 100 mg/day or wherein neramexane mesylate is administered at about 5 mg to about 75 mg/day or wherein neramexane mesylate is administered at about 50 mg/day or at about 75 mg/day.

A further aspect of the invention relates to such a method wherein the 1-amino-alkylcyclohexane derivative (e.g., neramexane) is administered once a day, twice a day (b.i.d.), or three times a day.

A further aspect of the invention relates to such a method, wherein the 1-amino-alkylcyclohexane derivative (e.g., neramexane) is administered twice a day.

A further aspect of the invention relates to such a method wherein the 1-amino-alkylcyclohexane derivative (e.g., neramexane) is administered in an immediate release formulation.

A further aspect of the invention relates to such a method wherein the 1-amino-alkylcyclohexane derivative (e.g., neramexane) is administered in an modified release formulation.

A further aspect of the invention relates to a pharmaceutical composition for the treatment of hearing loss comprising a therapeutically effective amount of a 1-amino-alkylcyclohexane derivative (e.g., neramexane), and at least one pharmaceutically acceptable carrier or excipient.

A further aspect of the invention relates to a pharmaceutical composition for the treatment or the prevention of hearing loss comprising a therapeutically effective amount of a 1-amino-alkylcyclohexane derivative (e.g., neramexane), and at least one pharmaceutically acceptable carrier or excipient.

A further aspect of the invention relates to a pharmaceutical composition for the treatment of hearing loss comprising a therapeutically effective amount of a 1-amino-alkylcyclohexane derivative (e.g., neramexane) in an immediate or modified release formulation.

A further aspect of the invention relates to the treatment of an individual diagnosed with hearing loss comprising administering to the individual a 1-amino-alkylcyclohexane derivative (e.g., neramexane) and at least one additional pharmaceutical agent which has been shown to be effective in treating hearing loss.

A further aspect of the invention relates to a method of treating or preventing hearing loss in a subject in need thereof, comprising administering an effective amount of a 1-amino-alkylcyclohexane derivative (e.g., neramexane) and an additional pharmaceutical agent which has been shown to be effective in treating or preventing hearing loss.

A further aspect of the invention relates to such a method wherein the 1-amino-alkylcyclohexane derivative (e.g., neramexane) and the additional pharmaceutical agent are administered conjointly.

A further aspect of the invention relates to such a method wherein the 1-amino-alkylcyclohexane derivative (e.g., neramexane) and the additional pharmaceutical agent are administered in a single formulation.

A further aspect of the invention relates to a pharmaceutical composition comprising a therapeutically effective amount of a 1-amino-alkylcyclohexane derivative (e.g., neramexane) in combination with an additional pharmaceutical agent which has been shown to be effective for the treatment or the prevention of hearing loss and, optionally, at least one pharmaceutically acceptable carrier or excipient.

A further aspect of the invention relates to a pharmaceutical composition comprising a therapeutically effective amount of a 1-amino-alkylcyclohexane derivative (e.g., neramexane) in combination with other therapies for hearing loss and, optionally, at least one pharmaceutically acceptable carrier or excipient.

BRIEF DESCRIPTION OF THE DRAWINGS

FIG. 1 shows the results of an analysis of change in hearing threshold following treatment with neramexane for 16 weeks.

DETAILED DESCRIPTION OF THE INVENTION

As used herein, the term hearing loss is synonymous with hearing impairment and includes several grades of hearing loss (such as mild hearing loss, moderate hearing loss, severe hearing loss, profound hearing loss, and deafness) as well as several specific forms, such as acoustic trauma, noise-induced hearing loss, sensorineural hearing loss, mixed hearing loss, unspecified hearing loss, ototoxic hearing loss, drug-induced hearing loss, sudden (idiopathic) hearing loss, auditory processing disorder, presbycusis, environmental chemicals-induced hearing loss, surgery-induced hearing loss, cancer-induced hearing loss, radiation-induced hearing loss, and infection-induced hearing loss.

The term 1-amino-alkylcyclohexane derivative is used herein to describe a compound which is a 1-amino-alkylcyclohexane or a compound derived from 1-amino-alkylcyclohexane, e.g. pharmaceutically acceptable salts of 1-amino-alkylcyclohexanes. The present 1-amino-alkylcyclohexane derivatives may also be described as "1-aminocyclohexane derivatives."

The 1-amino-alkylcyclohexane derivatives of the present invention may be represented by the general formula (I):

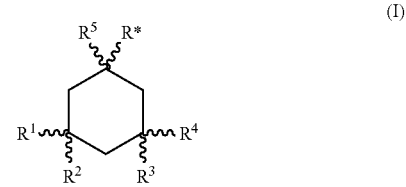

(I)

wherein R* is —$(CH_2)_n$—$(CR^6R^7)_m$—$NR^8R^9$
wherein n+m=0, 1, or 2
wherein $R^1$ through $R^7$ are independently selected from the group consisting of hydrogen and $C_{1-6}$alkyl, wherein $R^8$ and $R^9$ are independently selected from the group consisting of hydrogen and $C_{1-6}$alkyl or together represent lower-alkylene —$(CH_2)_x$— wherein x is 2 to 5, inclusive, and optical isomers, enantiomers, hydrates, and pharmaceutically-acceptable salts thereof.

Non-limiting examples of the 1-amino-alkylcyclohexanes used according to the present invention include:
1-amino-1,3,5-trimethylcyclohexane,
1-amino-1(trans),3(trans),5-trimethylcyclohexane,
1-amino-1(cis),3(cis),5-trimethylcyclohexane,
1-amino-1,3,3,5-tetramethylcyclohexane,
1-amino-1,3,3,5,5-pentamethylcyclohexane (neramexane),
1-amino-1,3,5,5-tetramethyl-3-ethylcyclohexane,
1-amino-1,5,5-trimethyl-3,3-diethylcyclohexane,
1-amino-1,5,5-trimethyl-cis-3-ethylcyclohexane,
1-amino-(1S,5S)cis-3-ethyl-1,5,5-trimethylcyclohexane,
1-amino-1,5,5-trimethyl-trans-3-ethylcyclohexane,
1-amino-(1R,5S)trans-3-ethyl-1,5,5-trimethylcyclohexane,
1-amino-1-ethyl-3,3,5,5-tetramethylcyclohexane,
1-amino-1-propyl-3,3,5,5-tetramethylcyclohexane,
N-methyl-1-amino-1,3,3,5,5-pentamethylcyclohexane,
N-ethyl-1-amino-1,3,3,5,5-pentamethyl-cyclohexane, N-(1,3,3,5,5-pentamethylcyclohexyl)pyrrolidine,
3,3,5,5-tetramethylcyclohexylmethylamine,
1 amino-1,3,3,5(trans)-tetramethylcyclohexane (axial amino group),
3-propyl-1,3,5,5-tetramethylcyclohexylamine semihydrate,
1-amino-1,3,5,5-tetramethyl-3-ethylcyclohexane,
1-amino-1,3,5-trimethylcyclohexane,
1-amino-1,3-dimethyl-3-propylcyclohexane,
1-amino-1,3(trans),5(trans)-trimethyl-3(cis)-propylcyclohexane,
1-amino-1,3-dimethyl-3-ethylcyclohexane,
1-amino-1,3,3-trimethylcyclohexane,
cis-3-ethyl-1(trans)-3(trans)-5-trimethylcyclohexamine,
1-amino-1,3(trans)-dimethylcyclohexane,
1,3,3-trimethyl-5,5-dipropylcyclohexylamine,
1-amino-1-methyl-3(trans)-propylcyclohexane,
1-methyl-3(cis)-propylcyclohexylamine,
1-amino-1-methyl-3(trans)-ethylcyclohexane,
1-amino-1,3,3-trimethyl-5(cis)-ethylcyclohexane,
1-amino-1,3,3-trimethyl-5(trans)-ethylcyclohexane,
cis-3-propyl-1,5,5-trimethylcyclohexylamine,
trans-3-propyl-1,5,5-trimethylcyclohexylamine,
N-ethyl-1,3,3,5,5-pentamethylcyclohexylamine,
N-methyl-1-amino-1,3,3,5,5-pentamethylcyclohexane,
1-amino-1-methylcyclohexane,
N,N-dimethyl-1-amino-1,3,3,5,5-pentamethylcyclohexane,
2-(3,3,5,5-tetramethylcyclohexyl)ethylamine,
2-methyl-1-(3,3,5,5-tetramethylcyclohexyl)propyl-2-amine,
2-(1,3,3,5,5-pentamethylcyclohexyl)-ethylamine semihydrate,
N-(1,3,3,5,5-pentamethylcyclohexyl)-pyrrolidine,
1-amino-1,3(trans),5(trans)-trimethylcyclohexane,
1-amino-1,3(cis),5(cis)-trimethylcyclohexane,
1-amino-(1R,5S)trans-5-ethyl-1,3,3-trimethylcyclohexane,
1-amino-(1S,5S)cis-5-ethyl-1,3,3-trimethylcyclohexane,
1-amino-1,5,5-trimethyl-3(cis)-isopropyl-cyclohexane,
1-amino-1,5,5-trimethyl-3(trans)-isopropyl-cyclohexane,
1-amino-1-methyl-3(cis)-ethyl-cyclohexane,
1-amino-1-methyl-3(cis)-methyl-cyclohexane,
1-amino-5,5-diethyl-1,3,3-trimethyl-cyclohexane,
1-amino-1,3,3,5,5-pentamethylcyclohexane,
1-amino-1,5,5-trimethyl-3,3-diethylcyclohexane,
1-amino-1-ethyl-3,3,5,5-tetramethylcyclohexane,
N-ethyl-1-amino-1,3,3,5,5-pentamethylcyclohexane,
N-(1,3,5-trimethylcyclohexyl)pyrrolidine or piperidine,
N-[1,3(trans),5(trans)-trimethylcyclohexyl]pyrrolidine or piperidine,
N-[1,3(cis),5(cis)-trimethylcyclohexyl]pyrrolidine or piperidine,
N-(1,3,3,5-tetramethylcyclohexyl)pyrrolidine or piperidine,
N-(1,3,3,5,5-pentamethylcyclohexyl)pyrrolidine or piperidine,
N-(1,3,5,5-tetramethyl-3-ethylcyclohexyl)pyrrolidine or piperidine,
N-(1,5,5-trimethyl-3,3-diethylcyclohexyl)pyrrolidine or piperidine,
N-(1,3,3-trimethyl-cis-5-ethylcyclohexyl)pyrrolidine or piperidine,
N-[(1S,5S)cis-5-ethyl-1,3,3-trimethylcyclohexyl]pyrrolidine or piperidine,
N-(1,3,3-trimethyl-trans-5-ethylcyclohexyl)pyrrolidine or piperidine,
N-[(1R,5S)trans-5-ethyl,3,3-trimethylcyclohexyl]pyrrolidine or piperidine,
N-(1-ethyl-3,3,5,5-tetramethylyclohexyl)pyrrolidine or piperidine,
N-(1-propyl-3,3,5,5-tetramethylcyclohexyl)pyrrolidine or piperidine,
N-(1,3,3,5,5-pentamethylcyclohexyl)pyrrolidine, and optical isomers, diastereomers, enantiomers, hydrates, their pharmaceutically acceptable salts, and mixtures thereof.

1-Amino-alkylcyclohexane derivatives (e.g., neramexane, 1-amino-1,3,3,5,5-pentamethylcyclohexane) are disclosed in U.S. Pat. Nos. 6,034,134 and 6,071,966. 1-Amino-alkylcyclohexane derivatives (e.g., neramexane) may be used according to the invention in the form of any of pharmaceutically acceptable salts, solvates, isomers, conjugates, and prodrugs, any references to 1-amino-alkylcyclohexane derivatives (e.g., neramexane) in this description should be understood as also referring to such salts, solvates, isomers, conjugates, and prodrugs.

Pharmaceutically acceptable salts include, but are not limited to, acid addition salts, such as those made with hydrochloric, methylsulfonic, hydrobromic, hydroiodic, perchloric, sulfuric, nitric, phosphoric, acetic, propionic, glycolic, lactic, pyruvic, malonic, succinic, fumaric, tartaric, citric, benzoic, carbonic, cinnamic, mandelic, methanesulfonic, ethanesulfonic, hydroxyethanesulfonic, benzenesulfonic, p-toluene sulfonic, cyclohexanesulfamic, salicyclic, p-aminosalicyclic, 2-phenoxybenzoic, and 2-acetoxybenzoic acid. All of these salts (or other similar salts) may be prepared by conventional means. The nature of the salt is not critical, provided that it is non-toxic and does not substantially interfere with the desired pharmacological activity.

The term "analog" or "derivative" is used herein in the conventional pharmaceutical sense, to refer to a molecule that structurally resembles a reference molecule (such as neramexane), but has been modified in a targeted and controlled manner to replace one or more specific substituents of the referent molecule with an alternate substituent, thereby generating a molecule which is structurally similar to the reference molecule. Synthesis and screening of analogs (e.g., using structural and/or biochemical analysis), to identify slightly modified versions of a known compound which may have improved or biased traits (such as higher potency and/or selectivity at a specific targeted receptor type, greater ability to penetrate mammalian blood-brain barriers, fewer side effects, etc.) is a drug design approach that is well known in pharmaceutical chemistry.

The term "treat" is used herein to mean to relieve or alleviate at least one symptom of a disease in a subject. Within the meaning of the present invention, the term "treat" also denotes to arrest, delay the onset (i.e., the period prior to clinical manifestation of a disease) and/or reduce the risk of developing or worsening a disease.

The term "therapeutically effective" applied to dose or amount refers to that quantity of a compound or pharmaceutical composition that is sufficient to result in a desired activity upon administration to a mammal in need thereof.

The phrase "pharmaceutically acceptable", as used in connection with compositions of the invention, refers to molecular entities and other ingredients of such compositions that are physiologically tolerable and do not typically produce untoward reactions when administered to a mammal (e.g., human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

The term "carrier" applied to pharmaceutical compositions of the invention refers to a diluent, excipient, or vehicle with which an active compound (e.g., neramexane) is administered. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Suitable pharmaceutical carriers are described in "Remington's Pharmaceutical Sciences" by A. R. Gennaro, 20$^{th}$ Edition.

The term "about" or "approximately" usually means within 20%, alternatively within 10%, including within 5% of a given value or range. Alternatively, especially in biological systems, the term "about" means within about a log (i.e., an order of magnitude), including within a factor of two of a given value.

In conjunction with the methods of the present invention, also provided are pharmaceutical compositions comprising a therapeutically effective amount of a 1-amino-alkylcyclohexane derivative (e.g., neramexane). The compositions of the invention may further comprise a carrier or excipient (all pharmaceutically acceptable). The compositions may be formulated for once-a-day administration, twice-a-day administration, or three times a day administration.

The active ingredient (e.g., neramexane) or the composition of the present invention may be used for the manufacture of a medicament for the treatment of at least one of the mentioned disorders, wherein the medicament is adapted to or appropriately prepared for a specific administration as disclosed herein (e.g., to once-a-day, twice-a-day administration, or three times a day administration). For this purpose the package leaflet and/or the patient information contains corresponding information.

According to the present invention, the dosage form of the 1-amino-alkylcyclohexane derivative (e.g., neramexane) may be a solid, semisolid, or liquid formulation according to the following.

The 1-amino-alkylcyclohexane derivatives of the present invention (e.g., neramexane) may be administered orally, topically, parenterally, or mucosally (e.g., buccally, by inhalation, or rectally) in dosage unit formulations containing conventional non-toxic pharmaceutically acceptable carriers. In another embodiment for administration to pediatric subjects, the 1-amino-alkylcyclohexane derivative may be formulated as a flavored liquid (e.g., peppermint flavor). The 1-amino-alkylcyclohexane derivatives of the present invention may be administered orally in the form of a capsule, a tablet, or the like, or as a semi-solid, or liquid formulation (see Remington's Pharmaceutical Sciences, 20$^{th}$ Edition, by A. R. Gennaro).

For oral administration in the form of a tablet or capsule, the 1-amino-alkylcyclohexane derivatives of the present invention (e.g., neramexane) may be combined with a non-toxic, pharmaceutically acceptable excipients such as binding agents (e.g., pregelatinized maize starch, polyvinylpyrrolidone or hydroxypropyl methylcellulose); fillers (e.g., lactose, sucrose, glucose, mannitol, sorbitol and other reducing and non-reducing sugars, microcrystalline cellulose, calcium sulfate, or calcium hydrogen phosphate); lubricants (e.g., magnesium stearate, talc, or silica, steric acid, sodium stearyl fumarate, glyceryl behenate, calcium stearate, and the like); disintegrants (e.g., potato starch or sodium starch glycolate); or wetting agents (e.g., sodium lauryl sulphate), coloring and flavoring agents, gelatin, sweeteners, natural and synthetic gums (such as acacia, tragacanth or alginates), buffer salts, carboxymethylcellulose, polyethyleneglycol, waxes, and the like.

The tablets may be coated with a concentrated sugar solution which may contain e.g., gum arabic, gelatine, talcum, titanium dioxide, and the like. Alternatively, the tablets can be coated with a polymer that dissolves in a readily volatile organic solvent or mixture of organic solvents. In specific embodiments, neramexane is formulated in immediate-release (IR) or modified-release (MR) tablets. Immediate release solid dosage forms permit the release of most or all of the active ingredient over a short period of time, such as 60 minutes or less, and make rapid absorption of the drug possible (immediate release formulations of 1-amino-alkylcyclohexanes such as neramexane are disclosed in US Published Application Nos. 2006/0002999 and 2006/0198884, the subject matter of which is hereby incorporated by reference). Modified release solid oral dosage forms permit the sustained release of the active ingredient over an extended period of time in an effort to maintain therapeutically effective plasma levels over similarly extended time intervals and/or to modify other pharmacokinetic properties of the active ingredient (modified release formulations of neramexane are disclosed in US Published Application No. 2007/0141148, the subject matter of which is hereby incorporated by reference). For example, neramexane mesylate may be formulated in a modified release dosage form (including modified release tablets) to provide a 50 mg dose of neramexane mesylate.

For the formulation of soft gelatin capsules, the 1-amino-alkylcyclohexane derivatives of the present invention (e.g., neramexane) may be admixed with e.g., a vegetable oil or poly-ethylene glycol. Hard gelatin capsules may contain granules of the active substances using either the above mentioned excipients for tablets e.g., lactose, saccharose, sorbitol, mannitol, starches (e.g., potato starch, corn starch or amylopectin), cellulose derivatives or gelatine. Also liquids or semisolids of the drug can be filled into hard gelatine capsules.

The 1-amino-alkylcyclohexane derivatives of the present invention (e.g., neramexane) can also be introduced in microspheres or microcapsules, e.g., fabricated from polyglycolic acid/lactic acid (PGLA) (see, e.g., U.S. Pat. Nos. 5,814,344; 5,100,669 and 4,849,222; PCT Publications No. WO 95/11010 and WO 93/07861). Biocompatible polymers may be used in achieving controlled release of a drug, include for example, polylactic acid, polyglycolic acid, copolymers of polylactic and polyglycolic acid, polyepsilon caprolactone, polyhydroxybutyric acid, polyorthoesters, polyacetals, polyhydropyrans, polycyanoacrylates, and cross-linked or amphipathic block copolymers of hydrogels.

Formulation of the 1-amino-alkylcyclohexane derivatives of the present invention in a semi-solid or liquid form may also be used. The 1-amino-alkylcyclohexane derivative (e.g., neramexane) may constitute between 0.1 and 99% by weight of the formulation, more specifically between 0.5 and 20% by weight for formulations intended for injection and between 0.2 and 50% by weight for formulations suitable for oral administration.

In one embodiment of the invention, the 1-amino-alkylcyclohexane derivative (e.g., neramexane) is administered in a modified release formulation. Modified release dosage forms provide a means for improving patient compliance and for ensuring effective and safe therapy by reducing the incidence of adverse drug reactions. Compared to immediate release dosage forms, modified release dosage forms can be used to prolong pharmacologic action after administration, and to reduce variability in the plasma concentration of a drug throughout the dosage interval, thereby eliminating or reducing sharp peaks.

A modified release form dosage may comprise a core either coated with or containing a drug. The core being is then coated with a release modifying polymer within which the drug is dispersed. The release modifying polymer disintegrates gradually, releasing the drug over time. Thus, the outer-most layer of the composition effectively slows down and thereby regulates the diffusion of the drug across the coating layer when the composition is exposed to an aqueous environment, i.e. the gastrointestinal tract. The net rate of diffusion of the drug is mainly dependent on the ability of the gastric fluid to penetrate the coating layer or matrix and on the solubility of the drug itself.

In another embodiment of the invention, the 1-amino-alkylcyclohexane derivative (e.g., neramexane) is formulated in an oral, liquid formulation. Liquid preparations for oral administration can take the form of, for example, solutions, syrups, emulsions or suspensions, or they can be presented as a dry product for reconstitution with water or other suitable vehicle before use. Preparations for oral administration can be suitably formulated to give controlled or postponed release of the active compound. Oral liquid formulations of 1-amino-alkylcyclohexanes, such as neramexane, are described in PCT International Application No. PCT/US2004/037026, the subject matter of which is hereby incorporated by reference.

For oral administration in liquid form, 1-amino-alkylcyclohexane derivatives of the present invention (e.g., neramexane) may be combined with non-toxic, pharmaceutically acceptable inert carriers (e.g., ethanol, glycerol, water), suspending agents (e.g., sorbitol syrup, cellulose derivatives or hydrogenated edible fats), emulsifying agents (e.g., lecithin or acacia), non-aqueous vehicles (e.g., almond oil, oily esters, ethyl alcohol or fractionated vegetable oils), preservatives (e.g., methyl or propyl-p-hydroxybenzoates or sorbic acid), and the like. Stabilizing agents such as antioxidants (BHA, BHT, propyl gallate, sodium ascorbate, citric acid) can also be added to stabilize the dosage forms. For example, solutions may contain from about 0.2% to about 20% by weight of neramexane, with the balance being sugar and mixture of ethanol, water, glycerol and propylene glycol. Optionally, such liquid formulations may contain coloring agents, flavoring agents, saccharine and carboxymethyl-cellulose as a thickening agent or other excipients.

In another embodiment, a therapeutically effective amount of a 1-amino-alkylcyclohexane derivative (e.g., neramexane) is administered in an oral solution containing a preservative, a sweetener, a solubilizer, and a solvent. The oral solution may include one or more buffers, flavorings, or additional excipients. In a further embodiment, a peppermint or other flavoring is added to the neramexane derivative oral liquid formulation.

For administration by inhalation, 1-amino-alkylcyclohexane derivatives (e.g., neramexane) of the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

Solutions for parenteral applications by injection may be prepared in an aqueous solution of a water-soluble pharmaceutically acceptable salt of the active substances, preferably in a concentration of from about 0.5% to about 10% by weight. These solutions may also contain stabilizing agents and/or buffering agents and may conveniently be provided in various dosage unit ampoules.

The formulations of the invention may be delivered parenterally, i.e., by intravenous (i.v.), intracerebroventricular (i.c.v.), subcutaneous (s.c.), intraperitoneal (i.p.), intramuscular (i.m.), subdermal (s.d.), or intradermal (i.d.) administration, by direct injection, via, for example, bolus injection or continuous infusion. Formulations for injection can be presented in unit dosage form, e.g., in ampoules or in multi-dose containers, with an added preservative. Alternatively, the active ingredient may be in powder form for reconstitution with a suitable vehicle, e.g., sterile pyrogen-free water, before use.

The invention also provides a pharmaceutical pack or kit comprising one or more containers containing a 1-amino-alkylcyclohexane derivative (e.g., neramexane) and, optionally, more of the ingredients of the formulation. In a specific embodiment, neramexane is provided as an oral solution (2 mg/ml) for administration with the use of a 2 teaspoon capacity syringe (dosage KORC®). Each oral syringe has blue hatch marks for measurement, with lines on the right side of the syringe (tip down) representing tsp units, and those on the left representing ml units.

The optimal therapeutically effective amount may be determined experimentally, taking into consideration the exact mode of administration, from in which the drug is administered, the indication toward which the administration is directed, the subject involved (e.g., body weight, health, age, sex, etc.), and the preference and experience of the physician or veterinarian in charge.

Dosage units for rectal application may be solutions or suspensions or may be prepared in the form of suppositories or retention enemas comprising neramexane in a mixture with a neutral fatty base, or gelatin rectal capsules comprising the active substances in admixture with vegetable oil or paraffin oil.

Toxicity and therapeutic efficacy of the compositions of the invention may be determined by standard pharmaceutical procedures in experimental animals, e.g., by determining the $LD_{50}$ (the dose lethal to 50% of the population) and the $ED_{50}$ (the dose therapeutically effective in 50% of the population). The dose ratio between therapeutic and toxic effects is the therapeutic index and it may be expressed as the ratio $LD_{50}/ED_{50}$. Compositions that exhibit large therapeutic indices are preferred.

Suitable daily doses of the active compounds of the invention in therapeutic treatment of humans are about 0.01-10 mg/kg bodyweight on peroral administration and 0.001-10 mg/kg bodyweight on parenteral administration. For example, for adults, suitable daily doses of neramexane (e.g. neramexane mesylate) are within the range from about 5 mg to about 150 mg per day, such as from about 5 mg to about 120 mg, from about 5 mg to about 100 mg, or from about 5 mg to about 75 mg, or from about 5 mg to about 50 mg, such as 25 mg or 50 mg, per day. An equimolar amount of another pharmaceutically acceptable salt, a solvate, an isomer, a conjugate, a prodrug or a derivative thereof, such as neramexane hydrochloride, is also suitable. For pediatric subjects aged 4-14, neramexane (e.g. neramexane mesylate) may be administered as an oral, liquid dosage form, at about 0.5 mg/day, up to a maximum dose of 10 mg/day.

The daily doses indicated herein may be administered, for example, as one or two dosing units once, twice or three times per day. Suitable doses per dosage unit may therefore be the daily dose divided (for example, equally) between the number of dosage units administered per day, and will thus typically be about equal to the daily dose or one half, one third, one quarter or one sixth thereof. Dosages per dosage unit may thus be calculated from each daily dosage indicated herein. A daily dose of 5 mg, for example may be seen as providing a dose per dosage unit of, for example, about 5 mg, 2.5 mg, 1.67 mg, 1.25 mg and 0.83 mg, depending upon the dosing regimen chosen. Correspondingly, a dosage of 150 mg per day corresponds to dosages per dosing unit of, for example, about 150 mg, 75 mg, 50 mg, 37.5 mg, and 25 mg for corresponding dosing regimens.

Treatment duration may be short-term, e.g., several weeks (for example 8-14 weeks), or long-term until the attending physician deems further administration no longer is necessary.

The 1-amino-alkylcyclohexane derivatives of the present invention (e.g., neramexane) may be administered as a monotherapy, or in combination with another agent prescribed for the treatment of hearing loss.

The term "combination" applied to active ingredients is used herein to define a single pharmaceutical composition (formulation) comprising two active agents (e.g., a pharmaceutical composition comprising a 1-amino-alkylcyclohexane derivative, such as neramexane, and another agent prescribed for the treatment of hearing loss) or two separate pharmaceutical compositions, each comprising an active agent (e.g. a pharmaceutical composition comprising a 1-amino-alkylcyclohexane derivative, such as neramexane, or another agent prescribed for the treatment of hearing loss), to be administered conjointly.

Within the meaning of the present invention, the term "conjoint administration" is used to refer to administration of 1-amino-alkylcyclohexane derivative, such as neramexane, and a second active agent (e.g. another agent prescribed for the treatment of hearing loss) simultaneously in one composition, or simultaneously in different compositions, or sequentially. For the sequential administration to be considered "conjoint", however, 1-amino-alkylcyclohexane derivative, such as neramexane, and the second active agent must be administered separated by a time interval which still permits the resultant beneficial effect for treating hearing loss in a mammal.

EXAMPLES

The following examples illustrate the invention without limiting its scope.

Example 1

Double Blind Placebo Controlled Pilot Trial of Neramexane for Treatment of Hearing Loss The objective of this pilot project is to conduct a clinical trial to assess the efficacy of neramexane as a treatment for hearing loss. Patients afflicted with various degrees of hearing loss being treated with neramexane may be expected to demonstrate an improvement in primary (e.g., change to baseline in hearing threshold level) and secondary (e.g., change to baseline in different frequencies on a pure tone audiogram) outcomes as compared to placebo treated patients. A hearing threshold level may be defined as the average of the pure tone hearing threshold levels at testing frequencies of 0.25, 0.5, 1, 2 and 4 kHz.

Study Design

The primary objective of this study is to investigate the safety and efficacy of neramexane mesylate at daily doses of up to 75 mg in the treatment of hearing loss in comparison to placebo.

Statistical Procedures and Populations for Analysis

In order to be eligible to participate in the study, patients must meet the following criteria:
- Male or female subjects aged between 18 and 80 years with diagnosed hearing loss of at least mild degree
- Signed written informed consent
- Female subjects must be at least 2 years post-menopausal or surgically sterile. Women of childbearing potential have to agree to use at least one effective method of contraception.

Subjects meeting any of the following criteria are excluded from the study:
- Subjects with a history of seizure disorders or receiving antiepileptic medication
- Hearing impairment related to disturbance of sound conduction (air conduction threshold more than 20 dB worse than in bone conduction in at least two tested frequencies)
- Former treatment with memantine, neramexane, amantadine or documented history of hypersensitivity or intolerance to NMDA antagonists
- Subjects who have uncontrolled systemic diseases (e.g. cardiac, renal, pulmonary, hepatic, or gastrointestinal) which might interfere with the trial
- Patients with a history of myocardial ischaemia/infarction within the last 6 months or cardiac insufficiency (NYHA II-IV))
- Subjects positive for HIV, hepatitis C or hepatitis B
- Subjects with abnormal laboratory, ECG or physical examination findings
- Subjects who are taking psychotropic drugs that cannot be discontinued
- Subjects who have been treated with a typical depot neuroleptic within six (6) months before screening.
- Subjects who plan to undergo elective surgery under local or general anaesthesia during the trial
- Subjects who have had a history of alcohol or substance abuse
- Current alcoholism, other substance abuse/dependence except nicotine or caffeine or subjects who test positive for non-authorised medication or substances on the urine substance screen
- Nursing women
- Subjects with no audiogram deficit and with normal hearing.
- Existence of any surgical or medical condition which might interfere with the pharmacokinetics of neramexane
- Subjects who are not euthyroid
- Subjects with a history of hepatic, cardiac, renal, neurologic, cerebrovascular, metabolic or pulmonary disease
- Subjects with history of cancer
- Subjects with a history of drug or other allergy
- Subjects who have recently used an investigational drug or recently participated in a trial
- Women who have a positive pregnancy test
- Female subjects who intend to get pregnant or male subjects who intend to father a child within the trial period The scheduled visits for evaluation of each patient are as follows:

Visit 1 (screening): After signing the consent form, the subject undergoes a neurological and otological evaluation. Pure-tone audiometry (bone and air conduction) is conducted. Patient eligibility for study is evaluated via a check of inclusion/exclusion criteria.

Visit 2 (baseline): The subjects are asked about adverse events and changes in concomitant medication/disease, which events/changes are documented. Subject is evaluated for study eligibility based on a review of the inclusion/exclusion criteria. Trial procedures as well as allowed and forbidden concomitant medications are reviewed with the subject. Subject is enrolled in the study and study medication (placebo or neramexane) is dispensed.

Visit 3: This visit occurs at the end of the first 2-week up-titration sequence. The patients are asked about adverse events and changes in concomitant medication/disease, which events/changes are documented. In addition, medication for the next 8 weeks will be dispensed.

Visit 4: This visit occurs at the end of the first 8-week fixed-dose double-blind treatment period, i.e. week 10. The patients are asked about adverse events and changes in concomitant medication/disease, which changes are documented. Pure-tone audiometry (air conduction) is conducted.

Visit 5 (week 16, end of treatment). This visit occurs at the end of the 14-week fixed-dose double-blind treatment period. The patients are asked about adverse events and changes in concomitant medication/disease, which changes are documented. Pure-tone audiometry (air conduction) is conducted.

Visit 7: This visit occurs at the end of the 4-week follow-up period after the last study medication dose. Review of concomitant medications as well as the occurrence of adverse events since the last visit is conducted with subject. Pure-tone audiometry including individual frequencies as well as hearing level of both ears is conducted.

Administration of Neramexane

Neramexane mesylate 25 mg modified release tablets and matching placebo tablets are administered as film coated tablets.

Neramexane mesylate (or placebo) is uptitrated to a maximum daily dose of 75 mg, starting with a daily dose of 25 mg for one week, and increasing dosage in 25 mg steps at weekly intervals.

Treatment is started in the evening of study day 1. The daily starting dose is 25 mg neramexane mesylate per dose to be taken for 7 days at bedtime. At day 8, the daily neramexane mesylate dose is increased to 50 mg for another 7 days (two tablets in the evening for one week). At day 15, patients are uptitrated to 75 mg neramexane mesylate. Patients continue to take neramexane for 13 weeks (three tablets once daily in the evening for 13). Patients who do not tolerate 75 mg per day may reduce the neramexane mesylate dose by 25 mg to 50 mg for the remainder of the total scheduled treatment duration. For example, patients who do not tolerate a 75 mg dose are allowed to step back to a 50 mg dose. Patients are then asked to stay on the 50 mg dose for the remainder of the total scheduled treatment duration of 7 weeks. This dosing regimen is shown in Table 1.

TABLE 1

Administration of Neramexane mesylate

| Treatment group | 2-week double-blind uptitration period | | 14-week fixed-dose double-blind period | 4-week follow-up |
|---|---|---|---|---|
| | 1 | 2 | 3-16 | 17-20 |
| Neramexane mesylate | 0/25 | 0/50 | 0/75 mg/d | — |
| Placebo | 0/0 | 0/0 | 0/0 | — |

Efficacy

Primary Outcome

Change from baseline in hearing threshold level of left/right ear (dB) calculated as average of the pure tone hearing level threshold levels at 0.25, 0.5, 1, 2 and 4 kHz.

Secondary Outcomes

Change from baseline in high frequency hearing threshold of left/right ear (dB) calculated as average of the pure tone hearing threshold levels at 4, 6, 8 and 10 kHz Change from baseline in individual frequencies (hearing thresholds) on a pure tone audiogram (air conduction)

Number of Responder

Patient-reported outcome on a 11-point Likert-Scale (0=hearing is not a problem, 10=hearing is a problem as much as possible)

Change in hearing impairment based on the hearing threshold level:

| | |
|---|---|
| no frequency hearing loss | <20 dB |
| mild hearing loss | 20-40 dB |
| moderate hearing loss | >40-70 dB |
| severe hearing loss | >70-95 dB |
| profound hearing loss | >95 dB |

Data Analysis

All efficacy analyses are based on the ITT population. All statistical tests used for testing the primary efficacy (confirmatory testing) and secondary efficacy criterions, and all statistical tests used for exploratory analyses are two-sided hypothesis tests performed at the 5% level of significance.

Discussion

The neramexane treated group demonstrates an improvement in primary outcomes as well as secondary outcomes as compared to the placebo group.

Example 2

Data from a Double Blind Placebo Controlled Pilot Trial of Neramexane

In a double-blind, multicenter, randomized, placebo-controlled, parallel-group study, the efficacy of neramexane in patients suffering from persistent, subjective uni- or bilateral tinnitus was assessed. Participants received either neramexane mesylate (e.g. 50 mg, as 25 mg immediate release tablets given twice daily) or placebo twice daily for 16 weeks. Neramexane mesylate was uptitrated in weekly steps of 12.5 or 25 mg during a 4-week uptitration period preceding the fixed-dose 12-week treatment period. Treatment was followed by a four week follow-up period.

A secondary efficacy analysis of the individual frequencies (hearing thresholds) on a pure tone audiogram (air conduction) unexpectedly showed a trend for a modest treatment effect compared to placebo after 16 weeks treatment for the 50 mg-dose group. These surprising results, which are shown in FIG. 1, demonstrate that neramexane may be useful in the treatment of hearing loss.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference.

The invention claimed is:

1. A method of treating hearing loss in a subject in need thereof, comprising oral administration of a 1-aminocyclohexane derivative selected from the group consisting of neramexane and pharmaceutically acceptable salts thereof, wherein the 1-aminocyclohexane derivative is administered at a dose of about 50 mg/day, and wherein treatment results in alleviation of at least one symptom of hearing loss.

2. The method of claim 1, wherein the hearing loss is selected from mild hearing loss, moderate hearing loss, severe hearing loss, profound hearing loss, and deafness.

3. The method of claim 1, wherein the hearing loss is selected from acoustic trauma, noise-induced hearing loss, sensorineural hearing loss, mixed hearing loss, unspecified hearing loss, ototoxic hearing loss, drug-induced hearing loss, environmental chemicals-induced hearing loss, cancer-induced hearing loss, surgical-induced hearing loss, radiation-induced hearing loss, infection-induced hearing loss, sudden (idiopathic) hearing loss, auditory processing disorder, and presbycusis.

4. The method of claim 1, wherein the 1-amino-alkylcyclohexane derivative is neramexane mesylate.

5. The method of claim 1, wherein neramexane or a pharmaceutically acceptable salt thereof is administered once a day, twice a day (b.i.d.), or three times a day.

6. The method of claim 5, wherein neramexane or a pharmaceutically acceptable salt thereof is administered twice a day.

7. The method of claim 1, wherein neramexane or a pharmaceutically acceptable salt thereof is administered in an immediate release formulation.

8. The method of claim 1, wherein neramexane or a pharmaceutically acceptable salt thereof is administered in a modified release formulation.

9. A method of treating hearing loss in a subject in need thereof, comprising oral administration a 1-aminocyclohexane derivative selected from the group consisting of neramexane and pharmaceutically acceptable salts thereof, wherein the 1-aminocyclohexane derivative is administered at a dose of about 50 mg/day, and an additional pharmaceutical agent which has been shown to be effective in treating hearing loss, wherein treatment results in alleviation of at least one symptom of hearing loss.

10. The method of claim 9, wherein the 1-amino-alkylcyclohexane derivative is neramexane mesylate.

* * * * *